United States Patent
An et al.

(10) Patent No.: US 9,856,723 B2
(45) Date of Patent: Jan. 2, 2018

(54) EXPERIMENT APPARATUS FOR ESTIMATING GROUND DEFORMATION DURING GAS HYDRATE RECOVERY

(71) Applicant: KOREA GAS CORPORATION, Gyeonggi-do (KR)

(72) Inventors: Seung Hee An, Gyeonggi-do (KR); Seong Min Lee, Seoul (KR); Young Soon Baek, Incheon (KR); Il Oh Kang, Gyeongsangnam-do (KR); Jeong Gyoo Kim, Gyeonggi-do (KR)

(73) Assignee: Korea Gas Corporation, Gyeonggi-do (KR)

( * ) Notice: Subject to any disclaimer, the term of this patent is extended or adjusted under 35 U.S.C. 154(b) by 187 days.

(21) Appl. No.: 14/408,555

(22) PCT Filed: Aug. 13, 2013

(86) PCT No.: PCT/KR2013/007296
§ 371 (c)(1),
(2) Date: Dec. 16, 2014

(87) PCT Pub. No.: WO2015/005523
PCT Pub. Date: Jan. 15, 2015

(65) Prior Publication Data
US 2016/0230521 A1    Aug. 11, 2016

(30) Foreign Application Priority Data
Jul. 11, 2013 (KR) .................. 10-2013-0081304

(51) Int. Cl.
*E02D 1/02* (2006.01)
*E21B 43/16* (2006.01)
(Continued)

(52) U.S. Cl.
CPC ............ *E21B 43/16* (2013.01); *E02D 1/02* (2013.01); *G01B 11/16* (2013.01); *G01N 1/2294* (2013.01);
(Continued)

(58) Field of Classification Search
CPC ........... E02D 1/02; E21B 43/16; G01B 11/16; G01N 1/2294; G01N 2001/2241; G01N 2001/2285
See application file for complete search history.

(56) References Cited

U.S. PATENT DOCUMENTS

| 4,744,650 A | * | 5/1988 | Becker | ............... G03B 39/00 352/84 |
| 2011/0319682 A1 | * | 12/2011 | Kang | ............... C07D 207/06 585/3 |
| 2012/0118586 A1 | | 5/2012 | Kameyama et al. | |

FOREIGN PATENT DOCUMENTS

| JP | 61-032663 U1 | 2/1986 |
| JP | 0721180 B2 | 3/1995 |

(Continued)

OTHER PUBLICATIONS

English only abstract of Japanese application No. 2006-010400, Jan. 12, 2006.
(Continued)

*Primary Examiner* — R. A. Smith
*Assistant Examiner* — John M Royston
(74) *Attorney, Agent, or Firm* — McDonnell Boehnen Hulbert & Berghoff LLP

(57) ABSTRACT

Disclosed herein is an experiment apparatus for estimating ground deformation during gas hydrate recovery. The experiment apparatus may include: a high-pressure cell having a space in which a sample containing gas hydrate is stored; a recovery member inserted into the sample so as to recover the gas hydrate contained in the sample to the (Continued)

outside; and a transparent region formed at one or more parts facing the space of the high-pressure cell, such that the sample stored in the space is observed from outside.

11 Claims, 5 Drawing Sheets

(51) Int. Cl.
    *G01B 11/16*     (2006.01)
    *G01N 1/22*     (2006.01)

(52) U.S. Cl.
    CPC ............... *G01N 2001/2241* (2013.01); *G01N 2001/2285* (2013.01)

(56) References Cited

FOREIGN PATENT DOCUMENTS

| | | | |
|---|---|---|---|
| JP | 2004245752 | A | 9/2004 |
| JP | 200610400 | A | 1/2006 |
| JP | 2007147428 | A | 6/2007 |
| JP | 5007378 | B2 | 8/2012 |
| KR | 1020100065610 | A | 6/2010 |
| WO | 2011/019053 | A1 | 2/2011 |

OTHER PUBLICATIONS

English only abstract of Japanese application No. 2007-147427, Jun. 14, 2007.

\* cited by examiner

[Figure 1]
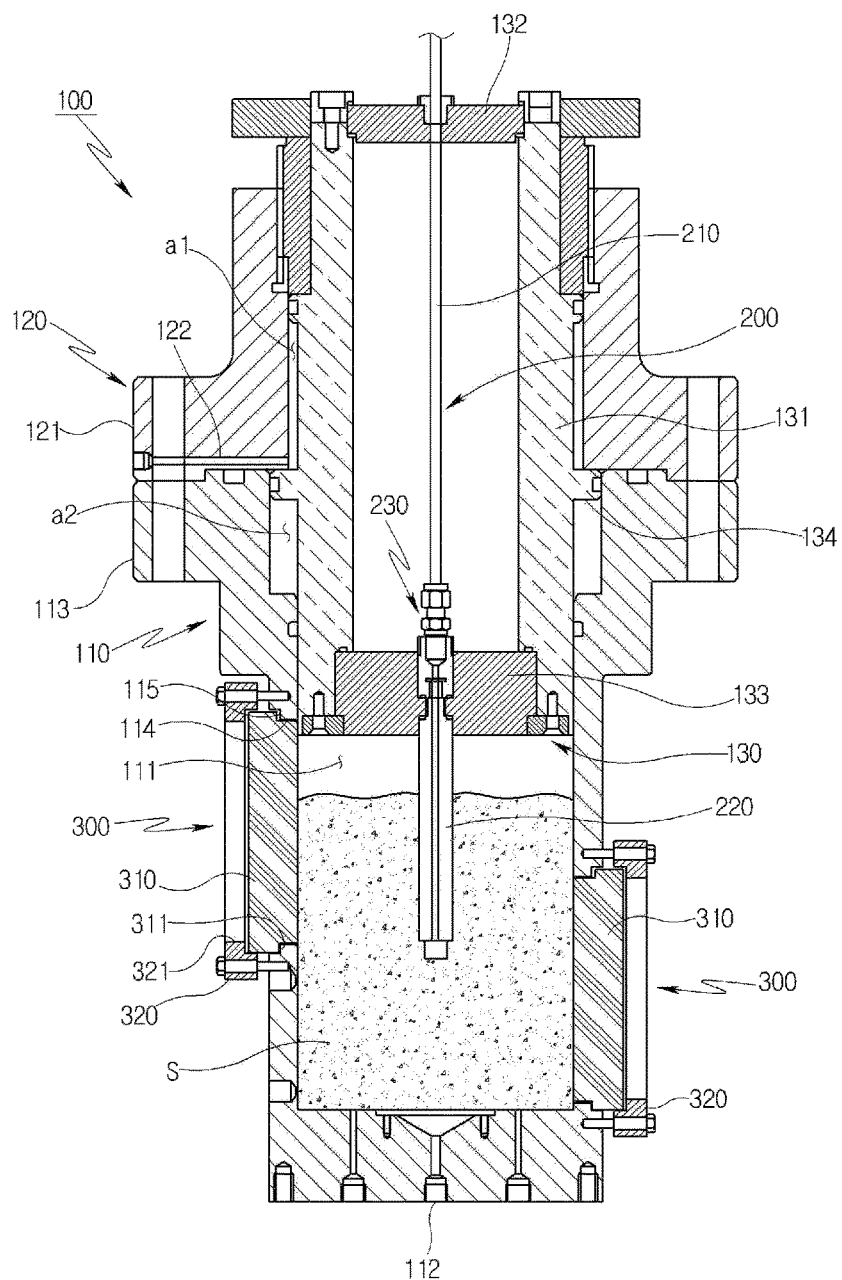

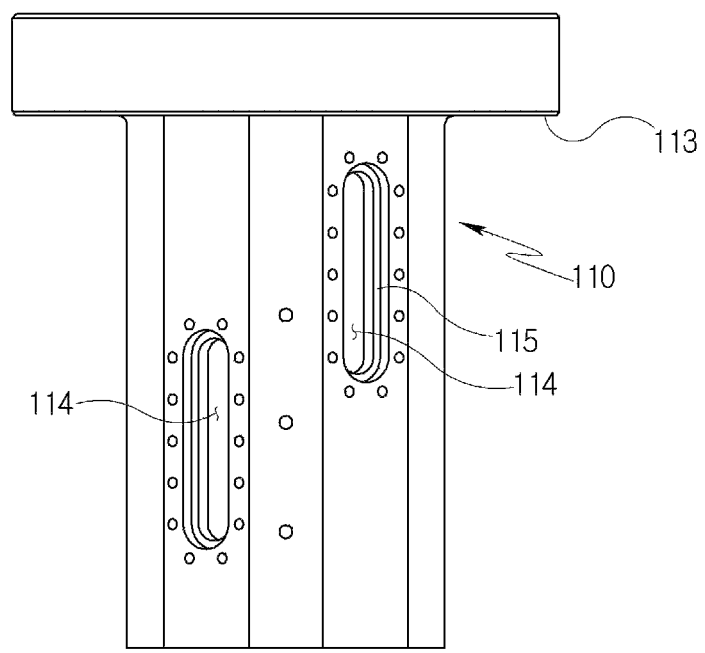
[Figure 2]

[Figure 3]
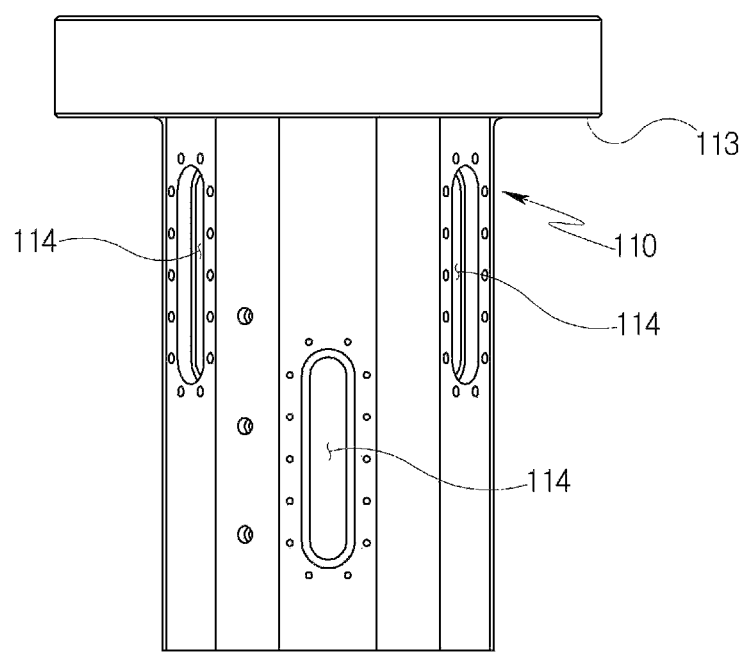

[Figure 4]
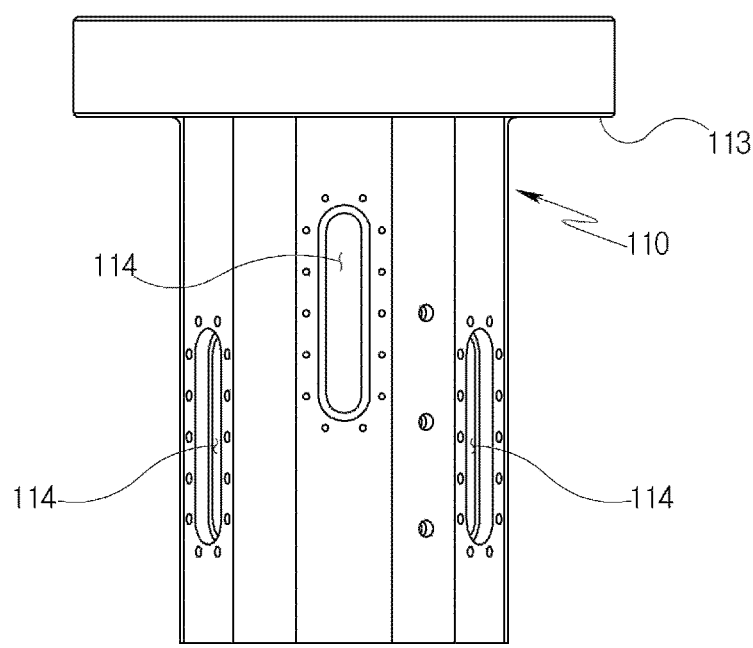

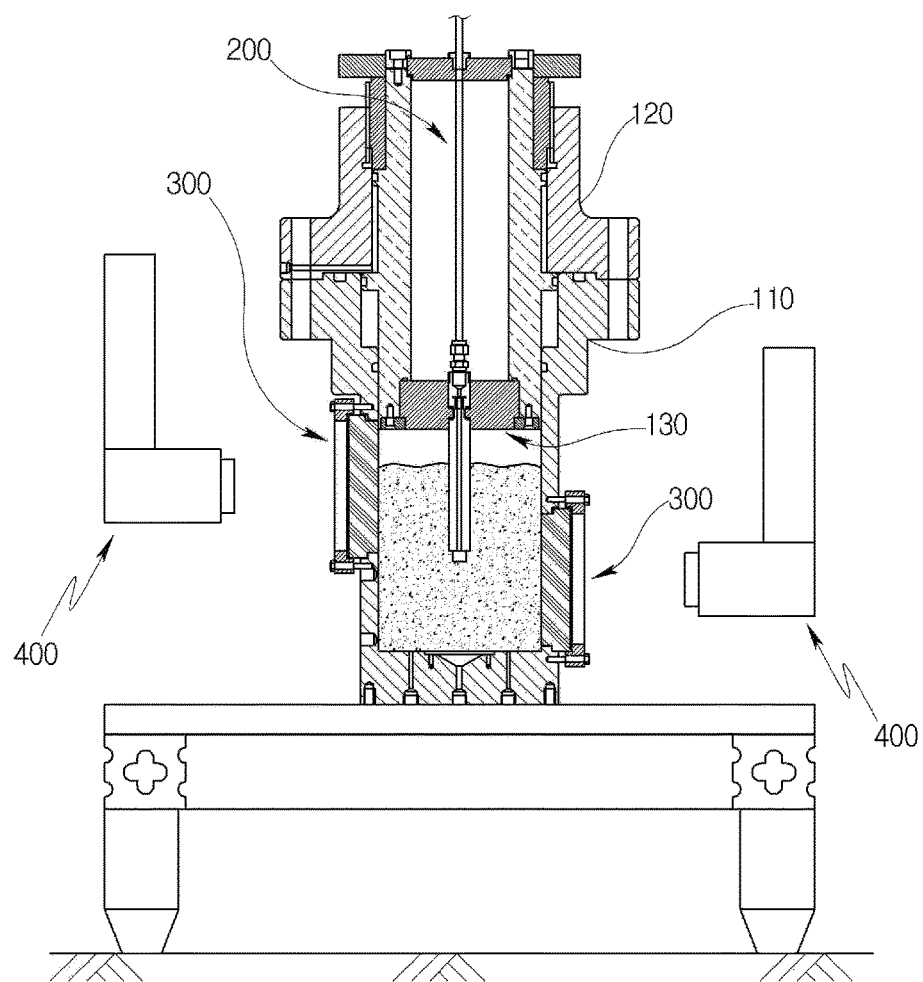
[Figure 5]

EXPERIMENT APPARATUS FOR ESTIMATING GROUND DEFORMATION DURING GAS HYDRATE RECOVERY

TECHNICAL FIELD

Exemplary embodiments of the present invention relate to an experiment apparatus for estimating ground deformation or ground subsidence which may occur when gas hydrate is recovered.

BACKGROUND ART

Gas hydrate refers to a solid material which is formed when gas such as methane (CH4) is combined with water molecules (H2O) at a low temperature and high pressure of 0° C. and 26 atmospheres or 10° C. and 76 atmospheres. Gas hydrate is easily found in an area adjacent to an oil or natural gas reservoir and a coal bed in a frozen soil region or a low-temperature and high-pressure deep-sea sedimentary layer, or particularly a continental slope.

In order to utilize such gas hydrate as a resource, an advanced mining technology must be applied. When the pressure is lowered, gas hydrate is dissociated while releasing methane. Thus, it is difficult to mine gas hydrate in a solid state like coal. As a method for extracting only methane by dissociating hydrate, various methods are used, which includes a depressurization method, a thermal injection method, an inhibitor injection method, a replacement method and the like.

According to the depressurization method, a borehole is formed in a free gas layer adjacent to gas hydrate so as to reduce the pressure of the gas layer. As the pressure of the free gas layer is reduced, the hydrate of the gas hydrate layer is dissociated to generate gas.

According to the thermal injection method, steam or hot water is injected to increase the temperature of a gas hydrate reservoir. Then, hydrate is dissociated to generate gas. The thermal injection method may be considered when there is no free gas layer adjacent to gas hydrate.

According to the inhibitor injection method based on a technology which is used to prevent hydration in a cold region, an additive such as methanol or glycol is injected to change a dissociation condition. When only the inhibitor injection method is used, a significant effect may not be obtained. However, when a hydraulic fracturing method and the thermal injection method are used at the same time, the effect of the inhibitor injection method is expected to be improved. However, the inhibitor injection method has disadvantages in that environmental pollution is likely to occur and the economic efficiency thereof is low due to a high cost required for a solvent used therein.

According to the replacement method which is a method for altering the molecular structure of gas hydrate, captured methane is extracted by replacing methane within gas hydrate with another material. When the replacement method is used, methane may be produced without melting a gas hydrate layer.

In addition, the method for extracting only methane by dissociating hydrate includes a geothermal stimulation method which generates hot water using ground heat and injects the generated hot water, and a controlled oxidation method which dissociates hydrate through a catalytic oxidation reaction in a stratum.

The region abundant in gas hydrate may be roughly divided into two regions. In general, a large amount of gas hydrate is found in the permanently-frozen soil and the continental slopes in the deep ocean. Depending on where gas hydrate is buried, the difficulty level of recovery may differ. For example, when gas hydrate exists in the hard rocks, ground deformation or ground subsidence hardly occurs while the gas hydrate is recovered. However, when gas hydrate exists in unconsolidated strata in the sea, ground deformation or ground subsidence may occur while the gas hydrate is recovered. Thus, it is important to previously analyze a ground deformation characteristic on gas hydrate recovery through an experiment, and to estimate the extent to which the strata is deformed, based on the result obtained through the experiment. In the current technical field related to gas hydrate, there has been proposed only a method and apparatus for recovering gas hydrate or an apparatus for artificially generating gas hydrate as disclosed in Korean Patent Laid-open Publication No. 10-2009-0122812. However, an experiment apparatus capable of estimating ground deformation through observation during gas hydrate recovery has not yet been disclosed.

DISCLOSURE

Technical Problem

The present invention has been made in view of the above problems, and it is an object of the present invention to provide an experiment apparatus for estimating ground deformation or ground subsidence during gas hydrate recovery, through observation by the naked eye of a sample stored therein.

Technical Solution

In accordance with one aspect of the present invention, an experiment apparatus may include: a high-pressure cell having a space in which a sample containing gas hydrate is stored; a recovery member inserted into the sample so as to recover the gas hydrate contained in the sample to the outside; and a transparent region formed at one or more parts facing the space of the high-pressure cell, such that the sample stored in the space is observed from outside.

The experiment apparatus may further include a photographing unit arranged outside the high-pressure cell so as to face the transparent region.

The transparent region may be formed of a different material from the high-pressure cell.

The transparent region may be formed of a material including sapphire.

The transparent region may be formed at a position where the surface of the sample stored in the space is observed.

The transparent region may be formed at a position where the inside of the sample stored in the space is observed.

The transparent region may be formed at a position where the surface of the sample stored in the space is observed and a position where the inside of the sample stored in the space is observed.

A plurality of transparent regions may be formed at predetermined intervals along the circumference of the high-pressure cell.

The transparent region may be formed by forming a through-hole at a part of the high-pressure cell, facing the space, and fixing a transparent member to the through-hole.

The transparent member may be formed of a material including sapphire.

The transparent member may be fixed to the high-pressure cell, while the edge of the transparent member is supported by a cover member coupled to the high-pressure cell.

DESCRIPTION OF DRAWINGS

The above and other objects, features and other advantages of the present invention will be more clearly understood from the following detailed description taken in conjunction with the accompanying drawings, in which:

FIG. 1 is a cross-sectional view of a high-pressure cell of an experiment apparatus according to an embodiment of the present invention;

FIGS. 2 to 4 are front views of a first body of the high-pressure cell illustrated in FIG. 1; and FIG. 5 illustrates an arrangement state of cameras in the experiment apparatus according to the embodiment of the present invention.

BEST MODE FOR INVENTION

Hereafter, embodiments of the present invention will be described with reference to the accompanying drawings.

The present invention may include various modifications and various embodiments, and thus specific embodiments will be illustrated in the drawings and described in the detailed descriptions. However, the present invention is not limited to specific embodiments, and may include all of variations, equivalents, and substitutes within the scope of the present invention.

The terms including technical or scientific terms have the same meanings as the terms which are generally understood by those skilled in the art to which the present invention pertains, as long as they are differently defined. The terms defined in a generally used dictionary may be analyzed to have meanings which coincide with contextual meanings in the related art. As long as the terms are not clearly defined in this specification, the terms may not be analyzed as ideal or excessively formal meanings.

Furthermore, the following embodiments are provided for clear understanding of those skilled in the art, and the shapes and sizes of components in the drawings are exaggerated for clarity of description.

FIG. 1 is a cross-sectional view of a high-pressure cell of an experiment apparatus according to an embodiment of the present invention. FIGS. 2 to 4 are front views of a first body of the high-pressure cell illustrated in FIG. 1. FIG. 5 illustrates an arrangement state of cameras in the experiment apparatus according to the embodiment of the present invention.

The experiment apparatus 1 for estimating ground deformation during gas hydrate recovery according to the embodiment of the present invention may include a high-pressure cell 100, a recovery member 200, and a transparent region 300. The high-pressure cell 100 may have a space 111 in which a sample S containing gas hydrate is stored. The recovery member 200 may be inserted into the sample S so as to recover the gas hydrate contained in the sample S to the outside. The transparent region 300 may be formed at one or more of parts facing the space 111 of the high-pressure cell 100 such that the sample S stored in the space 111 can be observed from outside.

The high-pressure cell 100 included in the experiment apparatus 1 according to the embodiment of the present invention may function as a component of an apparatus for generating and recovering gas hydrate as well as the component of the experiment apparatus for estimating ground deformation during gas hydrate recovery. The high-pressure cell 100 which can be used for generating and recovering gas hydrate or observing ground deformation during a recovery process may include a first body 110 and a second body 120.

In addition, the high-pressure cell 100 may further include a pressurizing member 130 to pressurize the sample S.

The first body 110 may be formed in a cylindrical shape, for example. The space 111 formed in the first body 110 may be opened upward, and the sample S for experiment may be stored in the space 111. The sample S may contain earth and sand such that ground deformation can be simulated. The sample S may already contain gas hydrate therein, or gas hydrate may be generated and contained in the sample S. The first body 110 may include a plurality of sensors (not illustrated) for measuring the pressure and temperature of the space 111. The first body 110 may have a first supply path 112 formed at one side thereof, for example, at the bottom thereof. Through the first supply path 112, water may be injected into the space 111. The first supply path 112 may be connected to a water tank (not illustrated) in which water is stored, and water supplied through the first supply path 112 may be supplied in a state where the water was cooled through a cooling device. For example, the supplied water may be cooled at a similar temperature to the internal temperature of the ground at an actual site. The first supply path 112 may be used as a supply path for methane gas which serves as a raw material for generating gas hydrate, as well as the supply path for water. For this structure, the first supply path 112 may be connected to a tank in which methane gas is stored. Furthermore, the first body 110 may have a first flange part 113 formed at the top thereof so as to be coupled to the second body 120 which will be described below.

The second body 120 may be coupled to the top of the first body 110. The second body 120 may be formed in a cylindrical shape, like the first body 110. The second body 120 may have a second flange part 121 formed at the bottom thereof, the second flange part 121 corresponding to the first flange part 113 of the first body 110. As the first and second flange parts 113 and 121 are stacked and coupled through a fastening member such as a bolt, the first and second bodies 110 and 120 may be coupled to each other. The second body 120 may also have a space formed therein. The internal space of the second body 120 may be opened in the upward direction, and communicate with the space 111 of the first body 110 in the downward direction.

The pressurizing member 130 may serve to pressurize the sample S stored in the space 111 of the first body 110. The pressurizing member 130 may be mounted to move upward and downward in the internal space of the second body 120. The pressurizing member 130 may include a hollow cylindrical body 131, a first cap 132 formed at the top of the cylindrical body 131, and a second cap 133 formed at the bottom of the cylindrical body 131. The second cap 133 may not only close the internal space of the cylindrical body 131 with respect to the bottom of the cylindrical body 131, but also form the bottom surface of the pressurizing member 130. In order that the sample S is stably pressurized by the pressurizing member 130 and the high-pressure state of the space 111 is maintained, there must be no clearance between the cylindrical body 131 and the space 111. Thus, the bottom part of the cylindrical body 131 may be formed to have the same outer diameter as the inner diameter of the space 111. At this time, since the internal space of the cylindrical body 131 is sealed by the second cap 133, the space 111 may be sealed by the bottom surface of the pressurizing member 130 with respect to the top side.

The cylindrical body 131 may have a protrusion 134 formed on the outer circumferential surface thereof, and the protrusion 134 may be formed along the circumferential direction the cylindrical body 131, while protruding in the diameter direction. The space between the inner circumferential surface of the second body 120 and the outer circumferential surface of the cylindrical body 131 may be divided into an upper space a1 and a lower space a2 by the protrusion 134. The second body 120 may have a second supply path 122 communicating with the upper space a1, and the second supply path 122 may be connected to a pump (not illustrated) which supplies fluid at high pressure. Through the second supply path 122, high-pressure fluid may be supplied to the upper space a1 so as to pressurize the cylindrical body 131 downward. As the cylindrical body 131 is pressurized downward, the pressurizing member 130 may be moved downward to pressurize the sample S.

The recovery member 200 may be mounted in the pressurizing member 130 so as to vertically penetrate the pressurizing member 130, and recover fluid including gas hydrate or gas hydrate and water contained in the sample S to the outside through an end thereof, which is inserted into the sample S. The recovery member 200 may include a flow path pipe 210, an insertion part 220, and a connection member 230. The flow path pipe 210 may be fixed to the first cap 132 while passing through the first cap 132, and extended to the vicinity of the second cap 133 along the longitudinal direction of the cylindrical body 131. The insertion part 220 may be extended downward such that a lower end thereof is positioned in the space 111 in a state where an upper end thereof is inserted and coupled to the bottom surface of the second cap 133 facing the sample S. The lower end of the flow path pipe 210 and the upper end of the insertion part 220 may be connected to each other by the connection member 230 which is inserted and fixed to the second cap 133. The insertion part 220 may have a flow path formed therein, the flow path communicating with a flow path of the flow path pipe 210. Thus, the gas hydrate or gas hydrate and water, recovered through the end of the insertion part 220, may be transferred to the outside through the flow path of the insertion part 220 and the flow path of the flow path pipe 210. The recovery member 200 may function as a supply path for supplying a raw material into the sample S, in order to generate or dissociate gas hydrate. That is, the flow path pipe 210 may be connected to a raw material supply tank (not illustrated) for gas hydrate, and a raw material for generating or dissociating gas hydrate may be supplied into the sample S through the flow path of the flow path pipe 210 and the flow path of the insertion part 220.

The experiment apparatus 1 according to the present embodiment may include the transparent region 300 through which an operator can observe deformation of the sample S, which occurs when the gas hydrate is recovered.

The transparent region 300, through which the sample S stored in the space 111 can be observed from outside the high-pressure cell 100, may be formed at one or more positions facing the space 111 of the high-pressure cell 100. More specifically, the transparent region 300 may be formed at one or more positions of the wall part of the first body 110, facing the space 111, in the entire region of the first body 110 having the space 111 formed therein. At this time, the transparent region 300 may be formed through the following process: a through-hole 114 is formed in the wall part of the first body 110 facing the space 111, and a transparent member 310 is fitted and fixed to the through-hole 114. The through-hole 114 may have a bump 115 formed on the inner surface thereof, and the transparent member 310 may also have a bump 311 formed on the circumferential surface thereof, the bump 311 corresponding to the bump 115 of the through-hole 114. Thus, the bump 311 formed on the circumferential surface of the transparent member 310 may be locked to the bump 115 of the through-hole 114 so as to limit the movement of the transparent member 310 into the high-pressure cell 100. Furthermore, the transparent member 310 may have a thickness to protrude from the outer surface of the first body 110 when the transparent member 310 is coupled to the through-hole 114. The transparent member 310 may be fixed to the first body 110 while supported by the cover member 320. Specifically, the cover member 320 may have a hole 321 formed in the center thereof so as not to interfere with observation through the transparent member 310. Furthermore, the cover member 320 may be fixed to the outer surface of the first body 110 while surrounding and supporting the edge of the transparent member 310. As the edge of the transparent member 310 is supported by the cover member 320, the movement of the transparent member 310 to the outside of the high-pressure cell 100 may be limited. The transparent member 310 may be supported by the locking structure of the above-described bumps 114 and 311 and the cover member 320 so as to be reliably fixed to the first body 110. However, the transparent member 310 is not limited thereto. The transparent member 310 may be fixed to the first body 110 through various structures.

The high-pressure cell 100 may form high pressure therein such that the sample S stored therein is placed under a similar condition to the ground of an actual site. The first and second bodies 110 and 120 forming the high-pressure cell 100 may be formed of stainless steel, for example, so as to endure high pressure. The transparent member 310 also needs to endure high pressure. Furthermore, the inside of the high-pressure cell 120 needs to be observed through the transparent member 310. Thus, the transparent member 310 may be formed of a different material from the first and second bodies 110 and 120. For example, the transparent member 310 may be formed of a material containing sapphire.

As illustrated in FIGS. 2 to 4, the transparent region 300 may be formed at a position where the surface of the sample S stored in the space 111 can be observed. Alternatively, the transparent region 300 may be formed at a position where the inside of the sample S can be observed. Alternatively, the transparent region 300 may be formed at positions where the surface and inside of the sample S can be observed. For example, the transparent region 300 may be formed at a position where the surface of the sample S can be observed and a position where the inside of the sample S can be observed. At this time, a plurality of transparent regions 300 may be formed at the above-described positions along the circumferential direction of the first body 110 such that the sample S can be observed in a plurality of directions along the circumferential direction of the high-pressure cell 100.

Thus, the deformation of the sample S may be observed with the naked eye through the transparent regions 300 of the experiment apparatus 1 according to the embodiment of the present invention. Furthermore, a photographing unit may be used to precisely analyze the deformation of the sample S and to store the analysis results as data. The photographing unit may include a high-sensitivity camera 400 which can take an image. As illustrated in FIG. 5, the camera 400 may be arranged outside the high-pressure cell 100 so as to face the transparent region 300. At this time, a plurality of cameras 400 may be arranged to correspond to the respective transparent regions 300, and controlled by a controller (not illustrated). The photographing unit may further a light source to brighten the inside of the sample S when an image is taken with the camera 400. Furthermore, the camera 400 may take an image of the inside of the space 111 through a laser shooting technique so as to reduce a decrease of light reflection in the space 111.

Hereafter, the process of the experiment apparatus having the above-described configuration will be described. First, the sample S may be stored in the space 111 of the first body 110 from which the second body 120 is removed, and the second body 120 and the pressurizing member 130 may be coupled to the top of the first body 110. Then, the pressurizing member 130 may be lowered to be contacted with the top surface of the sample S. During this process, the bottom part of the recovery member 200 may be inserted into the sample S. Then, water may be supplied into the space 111 through the first supply path 112 at the bottom of the first body 110, and the sample S in the space 111 may be set to a temperature and pressure condition of 6 to 8° C. and 1500 to 2000 psi and then pressurized to a pressure corresponding to a pressure of an actual site (for example, up to 3 MPa) by the pressurizing member 130. The pressure may be increased in steps by the pressurization. During such an operation, the temperature, the pressure, and the vertical displacement of the sample S may be monitored in real time. When the pressurization to the required pressure is completed, dissociation of gas hydrate may be induced, and gas extracted through the dissociation may be recovered through the recovery member 200.

During the recovery process through the recovery member 200, the deformation of the surface and inside of the sample S may be observed through the transparent region 300. The deformation of the sample S may be more precisely analyzed and stored as data through the camera 400.

According to the embodiment of the present invention, the experiment apparatus 1 may diversify the temperature and pressure condition applied to the sample S, the material forming the sample S, and the conditions related to the dissociation method and process and the recovery method for gas hydrate, and acquire information through which a ground deformation rate in an actual site can be precisely estimated.

While the present invention has been described with respect to the specific embodiments, it will be apparent to those skilled in the art that various changes and modifications may be made without departing from the spirit and scope of the invention as defined in the following claims.

INDUSTRIAL APPLICABILITY

According to the embodiment of the present invention, deformation of a sample during gas hydrate recovery may be observed with the naked eye or a camera and then analyzed and stored as data, the temperature or pressure condition within the high-pressure cell may be set to various conditions similar to those of an actual site, and an experiment may be performed to acquire information through which a ground deformation rate in an actual site can be precisely estimated.

The invention claimed is:
1. An experiment apparatus comprising:
 a high-pressure cell having a space in which a sample containing gas hydrate is stored;
 a recovery member inserted into the sample so as to recover the gas hydrate contained in the sample to the outside;
 a transparent member; and
 a transparent region formed at one or more parts facing the space of the high-pressure cell, such that the sample stored in the space is observed from outside,
 wherein the transparent region is formed by forming a through-hole at a part of the high-pressure cell, facing the space, and fixing the transparent member to the through-hole, the transparent member and high-pressure cell being different bodies, and
 the part of the high-pressure cell includes a portion that defines a first bump on an inner surface of the through-hole, and the transparent member includes a portion that defines a second bump along a circumference of the transparent member, where the second bump of the transparent member engages the first bump of the part of the high-pressure cell to limit movement of the transparent member into the high-pressure cell.
2. The experiment apparatus according to claim 1, further comprising a photographing unit arranged outside the high-pressure cell so as to face the transparent region.
3. The experiment apparatus according to claim 1, wherein the transparent member is formed of a different material from the high-pressure cell.
4. The experiment apparatus according to claim 1, wherein the transparent region is formed at a position where the surface of the sample stored in the space is observed.
5. The experiment apparatus according to claim 1, wherein the transparent region is formed at a position where the inside of the sample stored in the space is observed.
6. The experiment apparatus according to claim 1, wherein the transparent region is formed at a position where the surface of the sample stored in the space is observed and a position where the inside of the sample stored in the space is observed.
7. The experiment apparatus according to claim 1, wherein a plurality of transparent regions are formed at predetermined intervals along the circumference of the high-pressure cell.
8. The experiment apparatus according to claim 1, wherein the transparent member is formed of a material including sapphire.
9. The experiment apparatus according to claim 1, wherein the transparent member is fixed to the high-pressure cell, while the edge of the transparent member is supported by a cover member coupled to the high-pressure cell.
10. The experiment apparatus according to claim 1, wherein the first bump is formed from a same material as the part of the high-pressure cell defining the through-hole.
11. The experiment apparatus according to claim 1, wherein the second bump is formed from a same material as the transparent member.

* * * * *